United States Patent
Resconi et al.

[11] Patent Number: 6,051,728
[45] Date of Patent: Apr. 18, 2000

[54] METALLOCENE COMPOUNDS, PROCESS FOR THEIR PREPARATION, AND THEIR USE IN CATALYSTS FOR THE POLYMERIZATION OF OLEFINS

[75] Inventors: Luigi Resconi; Fabrizio Piemontesi, both of Ferrara, Italy; Ilya E. Nifant'ev; Pavel V. Ivchenko, both of Moscow, Russian Federation

[73] Assignee: Montell Technology Company BV, Hoofddorp, Netherlands

[21] Appl. No.: 08/599,483

[22] Filed: Jan. 23, 1996

[30] Foreign Application Priority Data

Jan. 23, 1995 [IT] Italy ................. MI95A0099

[51] Int. Cl.⁷ .............. C07F 17/00; C07F 9/00; C07F 7/00; C07F 11/00
[52] U.S. Cl. .............. 556/53; 556/11; 556/12; 556/14; 556/20; 556/43; 556/56; 556/58; 556/81; 556/160; 556/943; 502/103; 502/117
[58] Field of Search ................. 556/11, 43, 53, 556/56, 58, 12, 14, 20; 534/11, 15

[56] References Cited

U.S. PATENT DOCUMENTS

| | | | |
|---|---|---|---|
| 4,668,773 | 5/1987 | Marks et al. | 534/15 |
| 5,145,819 | 9/1992 | Winter et al. | 556/11 |
| 5,276,208 | 1/1994 | Winter et al. | 556/53 |
| 5,329,033 | 7/1994 | Spaleck et al. | 556/53 |
| 5,330,948 | 7/1994 | Marks et al. | 556/53 |
| 5,350,817 | 9/1994 | Winter et al. | 502/117 |
| 5,459,117 | 10/1995 | Ewen | 502/117 |
| 5,510,502 | 4/1996 | Sugano et al. | 556/58 |
| 5,532,396 | 7/1996 | Winter et al. | 556/58 |
| 5,693,836 | 12/1997 | Winter et al. | 556/11 |
| 5,696,045 | 12/1997 | Winter et al. | 556/11 |
| 5,703,257 | 12/1997 | Rosen et al. | 556/11 |
| 5,714,427 | 2/1998 | Winter et al. | 556/11 |
| 5,739,366 | 4/1998 | Imuta et al. | 556/11 |

FOREIGN PATENT DOCUMENTS

| | | |
|---|---|---|
| 2024718 | 3/1991 | Canada . |
| 2105914 | 3/1994 | Canada . |
| 2133181 | 3/1995 | Canada . |
| 0 129 368 A1 | 12/1984 | European Pat. Off. . |
| 0 351 392 A2 | 1/1990 | European Pat. Off. . |
| 0 416 566 | 3/1991 | European Pat. Off. . |
| 0 485 821 | 5/1992 | European Pat. Off. . |
| 0 485 823 | 5/1992 | European Pat. Off. . |
| 0 516 018 | 12/1992 | European Pat. Off. . |
| 0 588 208 | 3/1994 | European Pat. Off. . |
| 0 629 632 | 12/1994 | European Pat. Off. . |
| 0 645 401 | 3/1995 | European Pat. Off. . |

OTHER PUBLICATIONS

S. Miyake et al., Macromolecules, vol. 28, pp. 3074–3079, 1995.
J. Ewen, Macromol. Symp., vol. 89, pp. 181–196, 1995.
W. Spaleck et al., "Ziegler Catalysts", pp. 83–97, Springer Verlag, Berlin, 1995.
B. Peifer et al., J. Organomet. Chem., vol. 544, pp. 115–119, 1997.

(List continued on next page.)

*Primary Examiner*—Glenn Caldarola
*Assistant Examiner*—J. Pasterczyk
*Attorney, Agent, or Firm*—Bryan Cave LLP; Maurice B. Stiefel; Leo G. Lenna

[57] ABSTRACT

A class of metallocene compounds having two substituted cyclopentadienyl rings bridged by an alkylidene group wherein the cyclopentadienyl groups can be indenyl groups. The metallocene compounds have the following structures:

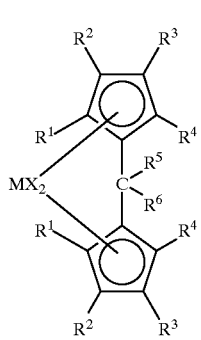

(I)

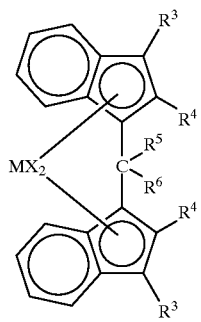

(II)

The metallocenes are characterized by three principal features: (i) the cyclopentadienyl groups are substituted at the 3-position with a substituent other than hydrogen, while $R^2$ in the 2-position bears a hydrogen (formula (I)) or is part of a condensed benzene ring (formula (II)); (ii) the bridge is a substituted-methylene bridge, i.e. a methylene group bearing at least one substituent other than hydrogen ($R^6$ is always different from hydrogen); and (iii) the cyclopentadienyl groups are identically substituted (page 2, line 23). These metallocene compounds can be suitably used as catalyst components for the polymerization of olefins. In particular, by polymerizing propylene in the presence of a catalyst based on these metallocene compounds, polymers having very high isotactic indexes, high molecular weights, and narrow molecular weight distributions can be obtained in high yields. A process for preparing the metallocenes from the corresponding organic ligands is also disclosed.

15 Claims, No Drawings

OTHER PUBLICATIONS

H. Luttikhedde et al., J. Organomet. Chem., vol. 547, pp. 129–132, 1997.

J. Ewen et al., Makromal. Chem., Macromol. Symp., vol. 48/49, pp. 253–295, 1991.

I.F. Urazowski et al., Xth Fechem Conference on Organometallic Chemistry, Sep. 5–10, 1993 in Agia Pelagia, Crete—Greece.

Macromolecules, 1995, vol. 28, pp. 6667–6676, L. Resconi et al.

Chemical Abstracts, vol. 123, No. 15, Oct. 19, 1995, Columbus, Ohio, U.S., abstract No. 199013, Urazowski, et al.

METALLOCENE COMPOUNDS, PROCESS FOR THEIR PREPARATION, AND THEIR USE IN CATALYSTS FOR THE POLYMERIZATION OF OLEFINS

The present invention relates to a class of bridged metallocene compounds, to the process for their preparation and to the use of these metallocenes as catalyst components for the polymerization of olefins.

Metallocene compounds with two bridged cyclopentadienyl groups are known as catalyst components for the polymerization of olefins.

For example, European Patent Application EP-A-129,368 describes a catalyst system for the polymerization of olefins which comprises a bis-cyclopentadienyl coordination complex with a transition metal, wherein the two cyclopentadienyl groups can be joined by a bridging group.

In this type of metallocene compounds the two cyclopentadienyl groups are generally bridged by divalent radicals having two or more carbon atoms, such as an ethylidene group, or with atoms other than carbon, such as a dimethylsilanediyl group.

Metallocene compounds having two cyclopentadienyl groups bridged by a single carbon atom are also known. In particular, metallocene compounds of this type having two different cyclopentadienyl groups are known.

For example, European Patent Application EP-A-351,392 describes a catalyst which can be used for the preparation of syndiotactic polyolefins and contains a metallocene compound with two cyclopentadienyl groups linked by a bridge between them, in which one of the two cyclopentadienyl groups is substituted in a manner different from that of the other. The compound indicated as being preferred is isopropylidene(fluorenyl)(cyclopentadienyl)hafnium dichloride.

As regards metallocene compounds having two equally substituted cyclopentadienyl groups bridged by a single carbon atom, in European Patent Application EP 416,566 it is described the polymerization of propylene, carried out in liquid monomer in the presence of a catalyst consisting of (A) an alumoxane and (B) a metallocene compound in which the cyclopentadienyl rings, which can be identical or different, are linked via a bridge of the formula —$R^5CR^6$— in which $R^5$ and $R^6$ can have different meanings. The only compound given as an example is isopropylidene-bis(indenyl)zirconium dichloride. However, the thus obtainable propylene polymers have a very low molecular weight.

I. F. Urazowski et al. at the Xth Fechem Conference on Organometallic Chemistry held on Sep. 5–10, 1993 in Agia Pelagia, Crete—Greece presented metallocene complexes of Ti and Zr obtained from two dicyclopentadienyl-dimethylmethanes, namely those having an isopropyl or tertbutyl substituent on the 3-position of each cyclopentadienyl ring. However, only mechanisms of the formation of those complexes and their structural features on the basis of X-ray analysis were discussed.

A novel class of metallocene compounds has now been found which has two identical cyclopentadienyl ligands which are linked to one another by an alkylidene bridge and which can advantageously be used as catalyst components for the polymerization of olefins.

An object of the present invention is therefore a metallocene compound of the formula (I):

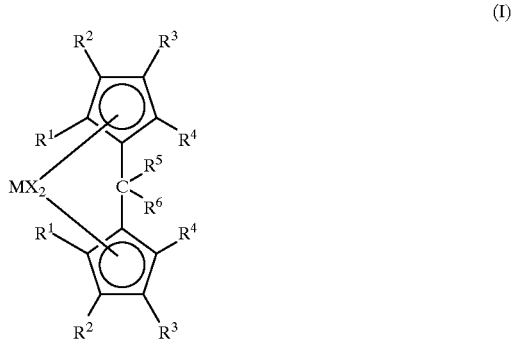

wherein $R^1$, $R^2$, $R^3$ and $R^4$ which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl groups which can contain silicon or germanium atoms, $R^3$ being different from $R^2$ and from a hydrogen atom, and wherein $R^1$ and $R^2$ on the same cyclopentadienyl ring can form a ring having 5 to 8 carbon atoms;

$R^5$ is a hydrogen atom or a —$CHR^7R^8$ group;

$R^6$ is a $C_6$–$C_{20}$-aryl radical or a —$CHR^9R^{10}$ group;

$R^5$ and $R^6$ can form a ring having 3 to 8 carbon atoms which can contain hetero atoms;

$R^7$, $R^8$, $R^9$ and $R^{10}$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals which can contain hetero atoms such as nitrogen, phosphorous, oxygen or sulphur, and two $R^7$, $R^8$, $R^9$ and $R^{10}$ substituents can form a ring having 3 to 8 carbon atoms which can contain hetero atoms;

M is an atom of a transition metal selected from those belonging to group 3, 4, 5, 6 or to the lanthanide or actinide groups in the Periodic Table of the Elements (new IUPAC version);

the X substituents, which can be identical or different, are hydrogen atoms, halogen atoms or R, OR, SR, $NR_2$ or $PR_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$-aryl, $C_7$–$C_{20}$-alkylaryl or $C_7$–$C_{20}$-arylalkyl radicals which can contain silicon or germanium atoms;

with the proviso that, when the $R^1$, $R^2$ and $R^4$ substituents are hydrogen atoms and the $R^5$ and the $R^6$ substituents are methyl groups, then the $R^3$ substituents are other than an isopropropyl or tertbutyl group.

The transition metal M is preferably selected from titanium, zirconium and hafnium and, more preferably, is zirconium.

The X substituents are preferably chlorine atoms or methyl radicals.

A particularly interesting class of metallocenes according to the invention is that of the compounds of the formula (I) in which the $R^2$ substituents are hydrogen atoms. The $R^1$ substituents are preferably different from hydrogen atoms. The $R^3$ substituents are preferably carbon, silicon or germanium atoms substituted with three alkyl, cycloalkyl, aryl, alkylaryl or arylalkyl groups having 1 to 10 carbon atoms. The $R^4$ substituents are preferably hydrogen atoms. Non-limiting examples of metallocene compounds belonging to this class are:

isopropylidene-bis(3-methyl-cyclopentadienyl)zirconium dichloride, isopropylidene-bis(3-isopropyl-cyclopentadienyl)zirconium dichloride, isopropylidene-bis(3-t-butyl-cyclopentadienyl)zirconium dichloride, isopropylidene-bis(2,4-dimethyl-cyclopentadienyl) zirconium dichloride, isopropylidene-bis(2-methyl-4-t-butyl-cyclopentadienyl) zirconium dichloride and isopropylidene-bis(2-methyl-4-phenyl-cyclopentadienyl) zirconium dichloride.

Another particularly interesting class of metallocenes according to the invention is that of the compounds of the formula (II):

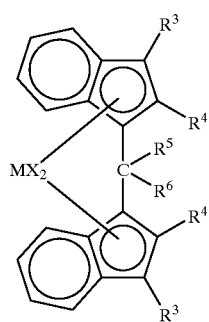

(II)

and the corresponding bis-4,5,6,7-tetrahydroindenyl compounds, wherein $R^3$, $R^4$, $R^5$, $R^6$, M and X are defined as above, and the six-carbon-atom rings of the indenyl ligands can optionally be substituted. The $R^3$ substituents are preferably carbon, silicon or germanium atoms substituted with three alkyl, cycloalkyl, aryl, alkylaryl or arylalkyl groups having 1 to 10 carbon atoms. The $R^4$ substituents are preferably hydrogen atoms. Non-limiting examples of metallocene compounds belonging to this class are:

isopropylidene-bis(3-methyl-indenyl)zirconium dichloride, isopropylidene-bis(3-ethyl-indenyl)zirconium dichloride, isopropylidene-bis(3-isopropyl-indenyl)zirconium dichloride, isopropylidene-bis(3-t-butyl-indenyl)zirconium dichloride, isopropylidene-bis(3-trimethylsilyl-indenyl)zirconium dichloride, isopropylidene-bis(3-trimethylgermyl-indenyl)zirconium dichloride, isopropylidene-bis(3-t-butyl-4,5,6,7-tetrahydroindenyl) zirconium dichloride.

The metallocene compounds of the formula (I) can be prepared by a process which represents another object of the present invention and which comprises the reaction of the corresponding bis-cyclopentadienyl ligands of the formula (III):

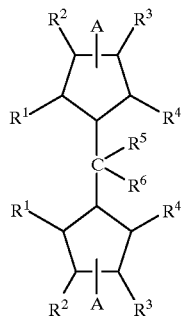

wherein $R^1$, $R^2$, $R^3$, $R^4$, $R^5$ and $R^6$ are defined as above, and A is a suitable leaving group, with a compound of the formula $MX_4$, wherein M and X are defined as above. The double bonds of the cyclopentadienyl rings in the ligands of formula (III) can be in any of the allowed positions. The ligands of the formula (III) can be prepared, for example, by the method described in the co-pending Italian Patent Application No. MI/95A/100 in the name of the same Applicant.

In the case in which at least one substituent X in the metallocene compound of the formula (I) which is to be prepared is other than a halogen, it is necessary to substitute at least one substituent X in the metallocene obtained by at least one substituent X other than a halogen.

The reaction of substituting substituents X by substituents X other than a halogen is carried out using generally applied methods. For example, if the desired substituents X are alkyl groups, the metallocenes can be made to react with alkyl-magnesium halides (Grignard reagents) or with alkyllithium compounds.

The metallocene compounds of the present invention can conveniently be used as catalyst components for the polymerization of olefins.

Still another object of the present invention is therefore a catalyst for the polymerization of olefins, consisting of the product of the reaction between:

(a) a metallocene compound according to the invention, and (b) an alumoxane or a compound able to form an alkyl-metallocene cation.

In the catalyst used in the process according to the invention, both the metallocene compound of the formula (I) and the alumoxane can be present as the product of the reaction with an organometallic aluminium compound of the formula $AlR^{11}_3$ or $Al_2R^{11}_6$, in which the substituents $R^{11}$ which can be identical or different are defined as for the substituents R or are halogen atoms.

The alumoxane used in the catalyst according to the invention is a linear, branched or cyclic compound containing at least one group of the type:

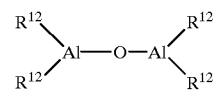

wherein the substituents $R^{12}$ which can be identical or different are defined as for the substituent R or are a group $-O-Al(R^{12})_2$ and, if appropriate, some $R^{12}$ can be halogen atoms.

In particular, alumoxanes of the formula:

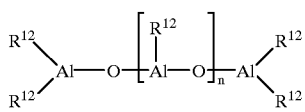

can be used in the case of linear compounds, wherein n is 0 or an integer of between 1 and 40 and the substituents $R^{12}$ are defined as for the substituents R, or alumoxanes of the formula:

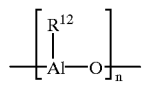

can be used in the case of cyclic compounds, with n being an integer of between 2 and 40 and the substituents $R^{12}$ being defined as for the substituents R.

The substituents $R^{12}$ are preferably methyl, ethyl, isobutyl or 2,4,4-trimethyl-pentyl.

Examples of alumoxanes suitable for use according to the present invention are methylalumoxane (MAO), isobutylalumoxane (TIBAO) and 2,4,4-trimethyl-pentylalumoxane (TIOAO).

Non-limiting examples of aluminium compounds of the formula $AlR^{11}_3$ or $Al_2R^{11}_6$ are:

Al(Me)$_3$, Al(Et)$_3$, AlH(Et)$_2$, Al(iBu)$_3$, AlH(iBu)$_2$, Al(iHex)$_3$, Al(iOct)$_3$, Al(C$_6$H$_5$)$_3$, Al(CH$_2$C$_6$H$_5$)$_3$, Al(CH$_2$CMe$_3$)$_3$, Al(CH$_2$SiMe$_3$)$_3$, Al(Me)$_2$iBu, Al(Me)$_2$ Et, AlMe(Et)$_2$, AlMe(iBu)$_2$, Al(Me)$_2$iBu, Al(Me)$_2$Cl, Al(Et)$_2$Cl, AlEtCl$_2$ and Al$_2$(Et)$_3$Cl$_3$, wherein Me=methyl, Et=ethyl, iBu=isobutyl and iHex=isohexyl, iOct=2,4,4-trimethyl-pentyl.

Amongst the above aluminium compounds, trimethylaluminium (TMA) and triisobutylaluminium (TIBAL) are preferred.

Non-limiting examples of compounds able to form an alkylmetallocene cation are compounds of the formula $Y^+Z^-$, wherein $Y^+$ is a Brönsted acid, able to donate a proton and to react irreversibly with a substituent X of the compound of the formula (I), and $Z^-$ is a compatible anion which does not coordinate and which is able to stabilize the active catalytic species which results from the reaction of the two compounds and which is sufficiently labile to be displaceable by an olefin substrate. Preferably, the anion $Z^-$ consists of one or more boron atoms. More preferably, the anion $Z^-$ is an anion of the formula BAr$_4$ ($^-$), wherein the substituents Ar which can be identical or different are aryl radicals such as phenyl, pentafluorophenyl or bis(trifluoromethyl)phenyl. Tetrakispentafluorophenyl borate is particularly preferred. Moreover, compounds of the formula BAr$_3$ can conveniently be used.

The catalysts of the present invention can also be used on inert supports. This is achieved by depositing the metallocene compound (A) or the product of the reaction thereof with the component (B), or the component (B) and then the metallocene compound (A) on inert supports such as, for example, silica, alumina, styrene/divinylbenzene copolymers or polyethylene.

The solid compound thus obtained, in combination with the further addition of the alkylaluminium compound either as such or prereacted with water if necessary, is usefully employed in gas-phase polymerization.

A further object of the present invention is a process for the polymerization of olefins, which comprises the polymerization reaction of one or more olefin monomers in the presence of a catalyst as described above.

Preferred olefin monomers are ethylene, the α-olefins and the cycloolefins. The catalysts according to the invention can conveniently be used, for instance, in the homopolymerization reactions of ethylene or of α-olefins such as propylene and 1-butene, in the copolymerization reactions of ethylene with α-olefins such as propylene and 1-butene, and also in the copolymerization reactions of propylene with C$_4$–C$_{10}$ α-olefins such as 1-butene. Particularly interesting results are achieved when the catalysts of the invention are used for the polymerization of propylene.

Thus, according to an embodiment of the process for olefin polymerization of the invention, propylene is polymerized in the presence of a metallocene compound of the formula (II), wherein the $R^3$ substituents are carbon, silicon or germanium atoms substituted with three alkyl, cycloalkyl, aryl, alkylaryl or arylalkyl groups having 1 to 10 carbon atoms, and wherein $R^4$, $R^5$, $R^6$, M and X are defined as above. The $R^4$ substituents are preferably hydrogen atoms. Examples of those metallocene compounds are:

isopropylidene-bis(3-t-butyl-indenyl)zirconium dichloride,
isopropylidene-bis(3-trimethylsilyl-indenyl)zirconium dichloride, and
isopropylidene-bis(3-trimethylgermyl-indenyl)zirconium dichloride.

The thus obtainable propylene polymers have narrow molecular weight distributions coupled with high isotactic indexes and a very high levels of regioregularity. In fact, the $^{13}$C-NMR analysis carried out on these polymers does not show structural units due to regioirregular insertions. Reference is made to "Macromolecules, 1995, vol.28, pagg. 6667–6676".

Thus, another object of the present invention is a propylene homopolymer having the following characteristics:

molecular weight distribution (Mw/Mn) lower than 4, preferably lower than 3.5, more preferably lower than 3, isotactic (mmmm) pentads, as determined by $^{13}$C-NMR analyses, higher than 70%, preferably comprised between 75 and 97%, more preferably between 80 and 95%, no structural units due to regioirregular insertions detectable at the $^{13}$C-NMR analysis carried out with a 300 MHz instrument.

If the polymerization of propylene is carried out in the presence of a bis-4,5,6,7-tetrahydroindenyl metallocene compound corresponding to the above said compounds of the formula (II), a very low molecular weight polypropylene wax is obtained. Notwithstanding the low molecular weight, these waxes have fairly high isotactic indexes as demonstrated by the presence of a melting point and by the values of isotactic (m) diads, as determined by $^{13}$C-NMR analyses, which are generally higher than 90%.

According to another embodiment of the process for olefin polymerization of the invention, propylene is polymerized in the presence of a metallocene compound of the formula (I) in which the $R^2$ substituents are hydrogen atoms and the $R^3$ substituents are carbon, silicon or germanium atoms substituted with three alkyl, cycloalkyl, aryl, alkylaryl or arylalkyl groups having 1 to 10 carbon atoms. The $R^4$ substituents are preferably hydrogen atoms. Examples of those metallocene compounds are:

isopropylidene-bis(3-t-butyl-cyclopentadienyl)zirconium dichloride, and
isopropylidene-bis(2-methyl-4-t-butyl-cyclopentadienyl) zirconium dichloride.

The thus obtainable propylene polymers, besides narrow molecular weight distributions, have very high isotactic indexes, as results from their high melting points which are generally higher than 155° C. and also higher than 160° C.

Thus, a further object of the present invention is a propylene homopolymer having the following characteristics:

molecular weight distribution (Mw/Mn) lower than 4, preferably lower than 3.5, more preferably lower than 3, isotactic (m) diads, as determined by $^{13}$C-NMR analyses, higher than 99%, preferably higher than 99.5%.

Even the values of isotactic (mmmm) pentads for these polymers can be as high as 99% and over.

These polymers do not have a very high level of regio-regularity. In fact, the $^{13}$C-NMR analysis carried out with a 300 MHz instrument on these polymers generally shows the presence of a low amount of structural units due to regio-irregular insertions, such as 1,3 insertions.

Particularly interesting results are achieved when in the above said specific metallocene compounds of the formula (I) the $R^1$ substituents are different from hydrogen atoms, such as for the isopropylidene-bis(2-methyl-4-t-butyl-cyclopentadienyl)zirconium dichloride. It is thus possible to obtain propylene polymers having very high isotactic indexes, as results from their melting points which can be higher than 160° C. even at polymerization temperatures of industrial interest, such as 50° C. and higher.

The propylene polymers obtainable from the process of the invention have low xylene-soluble fractions, generally lower than 5% by weight, preferably lower than 3% by weight, more preferably lower than 1% by weight.

The polymerization reaction of propylene according to the invention can be carried out in the presence of a $C_4$–$C_{10}$ α-olefin comonomer, such as 1-butene. It is thus possible to obtain propylene copolymers with 0.1–10% by moles of a $C_4$–$C_{10}$ α-olefin comonomer having characteristics similar to those of the corresponding homopolymer but a lower melting point. Notwithstanding the presence of a comonomer, these copolymers still have an extremely low xylene-soluble fractions, generally lower than 3% by weight, preferably lower than 2% by weight, more preferably lower than 1% by weight.

Thus, a still further object of the present invention is a propylene copolymers with 0.1–10% by moles of a $C_4$–$C_{10}$ α-olefin comonomer, preferably 1-butene, having the following characteristics:

isotactic (m) diads, as determined by $^{13}$C-NMR analyses, higher than 70%, preferably higher than 75%, more preferably higher than 80%, molecular weight distribution (Mw/Mn) lower than 4, preferably lower than 3.5, more preferably lower than 3, xylene-soluble fractions lower than 3% by weight, preferably lower than 2% by weight, more preferably lower than 1% by weight.

The process for the polymerization of olefins according to the invention can be carried out in the liquid phase in the presence or absence of an inert hydrocarbon solvent, or in the gas phase. The hydrocarbon solvent can either be aromatic such as toluene, or aliphatic such as propane, hexane, heptane, isobutane or cyclohexane.

The polymerization temperature is generally comprised between –100° C. and +80° C., and more particularly between –50° C. and +50° C. The lower the polymerization temperature, the higher are the resulting molecular weights of the polymers obtained.

The molecular weight of the polymers can be also varied by varying the type or the concentration of the catalyst components or using molecular weight regulators such as, for example, hydrogen.

The molecular weight distribution can be varied by using mixtures of different metallocene compounds or by carrying out the polymerization in several stages at different polymerization temperatures and/or different concentrations of the molecular weight regulators.

The polymerization yields depend on the purity of the metallocene compound of the catalyst. The metallocene compounds obtained by the process of the invention can therefore be used as such or can be subjected to purification treatments.

The components of the catalyst can be put into contact with one another before the polymerization. The contact time is generally between 1 and 60 minutes, preferably between 5 and 20 minutes. The pre-contact concentrations are between $10^{-2}$ and $10^{-8}$ mol/l for the metallocene component (A), while they are between 10 and $10^{-3}$ mol/l for the component (B). The pre-contact is generally effected in the presence of a hydrocarbon solvent and, if appropriate, of small quantities of monomer.

The following examples are given for illustrative purposes and do not limit the invention.

CHARACTERIZATIONS

The $^1$H-NMR analyses were carried out on a Bruker 200 MHz instrument with a pulse amplitude of 400 and a 1 second interval between pulses. 128 to 512 data points were accumulated for each sample, depending on the solubility of the various compounds.

The $^{13}$C-NMR analyses were carried out on a Varian UNITY-300 instrument operating at 75.4 MHz. The samples were analyzed in a 15% solution in deuteroethane tetrachloride at 130° C. For each sample, 6000 data points were accumulated with an interval of 12 seconds between each pulse.

The intrinsic viscosity (η) is measured in tetralin at 135° C.

Measures of Differential Scanning Calorimetry (D.S.C.) were carried out on an instrument DSC-7 of Perkin Elmer Co. Ltd., according to the following method. About 10 mg of sample obtained from the polymerization were cooled to –25° C. and thereafter heated at 200° C. with a scanning speed corresponding to 10° C. minute. The sample was kept at 200° C. for 5 minutes and thereafter cooled with a scanning speed corresponding to 10° C. minute. Then, a second scanning was carried out according to the same modalities of the first one. The values reported are those obtained in the first scanning.

The distribution of molecular weights was determined by GPC carried out on an instrument WATERS 150 in orthodichlorobenzene at 135° C.

The solubility in xylene of the propylene polymers is determined by dissolving 2 g of polymer in 250 ml of xylene at 135° C. and stirring the system. After 20 minutes, the solution is cooled down to 25° C. After 30 minutes the precipitated material is filtered; the solution is evaporated in nitrogen flow and the residue is dried at 80° C. In this way the percentage of polymer soluble in xylene at room temperature (XSRT) is calculated and thus also the percentage of insoluble polymer.

PREPARATION OF THE METALLOCENES

All the operations were carried out in a dry nitrogen atmosphere, using the conventional techniques for the handling of compounds which are sensitive to air.

THF=tetrahydrofuran
Et$_2$O=ethyl ether
DME=dimethoxyethane

EXAMPLE 1 rac-isopropylidene-bis(3-trimethylsilyl-indenyl) zirconium dichloride (a) Synthesis of 2,2-bis(indenyl)propane 23.5 ml (200 mmol) of indene was added within 0.5 hours to a suspension of 15 g of milled KOH in 150 ml of DME. The mixture was heated to reflux. Then 7.5 ml (100 mmol) of acetone was added dropwise within 0.5 hours and the mixture was stirred under reflux for additional 2 hours. The resulting mixture was cooled, treated with 200 ml of diluted phosphoric acid until neutralization and then with 100 ml of diethyl ether. The organic layer was separated, washed with water and dried over Na$_2$SO$_4$. Then the solvent was removed in vacuo and the residue was distilled at 130–160° C. and 0.01 torr. The broad fraction was collected and recrystallized from a 1:1 ether/hexane mixture, thus obtaining 20.4 g of the product (yield 72%). $^1$H-NMR (acetone-d$_8$, 30° C.) δ: 7.37 (d,2H); 7.32 (d,2H); 6.98 (m,4H); 6.60 (t,2H)) {=CH—} 3.38 (d,4H, —CH$_2$—) 1.74 (s,6H, —CH$_3$).

(b) Synthesis of 2.2-bis(3-trimethylsilyl-indenyl)propane 5.45 g (20 mmol) of 2,2-bis(indenyl)propane was dissolved in 100 ml of ether. The solution thus obtained was taken to –20° C., and 22 ml of a 2.0 M solution of n-butyl-lithium in pentane was added, thus giving a suspension of dilithium-2,2-(indenyl)propane. 8.77 g (30.85 mmol) of dilithium 2,2-bis(indenyl)propane was dissolved in 100 ml of ether, and 10 ml of Me$_3$SiCl (excess) was added at a temperature of –40° C. The resulting mixture was allowed to return to room temperature. The organic phase was then separated off, the solvent removed and the product dried in vacuo.

(c) Synthesis of rac-isopropylidene-bis(3-trimethylsilyl-indenyl)zirconium dichloride 8.34 g (20 mmol) of 2,2-bis(3-trimethylsilyl-indenyl) propane were dissolved in 100 ml of ether. The solution thus obtained was taken to –20° C., and 22 ml of a 2.0 M solution of n-butyl-lithium in pentane were added, a suspension of the dilithium 2,2-bis(3-trimethylsilyl-indenyl)propane thus being obtained. To this suspension, which was first allowed to rise to room temperature and was then cooled to –40° C., 12.06 g (50 mmol) of triethylstannylchloride were added. The organic layer was separated off and subjected to evaporation, and 50 ml of toluene were then added. Subsequently, 4.66 g (20 mmol) of ZrCl$_4$ was added, and the mixture thus obtained was taken to 80° C. and stirred for a further 6 hours. The toluene was then removed, and the product was washed with DME (5×50 ml) and recrystallized from DME. 3.69 g of pure rac-isopropylidene-bis(3-trimethylsilyl-indenyl)zirconium dichloride was obtained (yield 32%). $^1$H-NMR (CD$_2$Cl$_2$, 30° C.) δ: 7.80 (d,2H); 7.55 (d,2H); 7.30 (t,2H); 7.06 (t,2H); 6.06 (s,2H); 2.38 (s,6H); 0.23 (s,18H).

EXAMPLE 2 rac-isopropylidene-bis(3-methyl-indenyl)zirconium dichloride (a) Synthesis of 2.2-bis(3-methyl-indenyl)propane It was worked according to the procedure described at point (a) of example 1 except that, instead of indene, 200 mmol of 3-methyl-indene was used and that, after the acetone addition, the mixture was stirred under reflux for 3 hours. The temperature of distillation was 135–165° C. The product was isolated as dilithium salt (yield 65%). $^1$H-NMR (THF-d$_8$, 30° C.) δ: 7.42 ("d",2H); 7.10 ("d",2H); 6.26 ("t",2H); 6.18 ("t",2H) {ABCD, J=9 Hz} 6.47 (s,2H); 2.33 (s,6H,Ind-CH$_3$); 1.90 (s,6H,>CMe$_2$).

(b) Synthesis of rac-isopropylidene-bis(3-methyl-indenyl) zirconium dichloride

It was worked according to the procedure described at point (c) of example 1 except that, instead of 2,2-bis(3-trimethylsilyl-indenyl)propane, 20 mmol of the dilithium salt of 2,2-bis(3-methyl-indenyl)propane was used, and that the product was recrystallized from toluene. Pure rac-isopropylidene-bis(3-methyl-indenyl)zirconium dichloride was obtained. $^1$H-NMR (CD$_2$Cl$_2$, 30° C.) δ: 7.64 (d,2H); 7.42 (d,2H); 7.22 (m,2H); 6.96 (m,2H); 5.83 (s,2H); 2.30 (s,6H); 2.28 (s,6H).

EXAMPLE 3 rac-isopropylidene-bis(3-ispropyl-indenyl)zirconium dichloride (a) Synthesis of 2,2-bis(3-isopropyl-indenyl)propane It was worked according to the procedure described at point (a) of example 1 except that, instead of indene, 200 mmol of 3-isopropyl-indene was used and that, after the acetone addition, the mixture was stirred under reflux for 4 hours. The temperature of distillation was 140–175° C. The product was isolated as dilithium salt (yield 63%). $^1$H-NMR (THF-d$_8$, 30° C.) δ: 7.45 ("d",2H) 7.27 ("d",2H) 6.30 ("t",2H) 6.23 ("t",2H) {ABCD, J=8.0 Hz} 6.63 (s,2H) 3.30 (sept, J=7.0 Hz,2H,—CH(CH$_3$)$_2$); 1.98 (s, 6H,>CMe$_2$) 1.35 (d,J=7.0 Hz, 12H, —CH(CH$_3$)$_2$).

(b) Synthesis of rac-isopropylidene-bis(3-isopropyl-indenyl)zirconium dichloride It was worked according to the procedure described at point (c) of example 1 except that, instead of 2,2-bis(3-trimethylsilyl-indenyl)propane, 20 mmol of the dilithium salt of 2,2-bis(3-isopropyl-indenyl)propane was used, and that the product was recrystallized from DME. Pure rac-isopropylidene-bis(3-isopropyl-indenyl)zirconium dichloride was obtained. $^1$H-NMR (toluene-d$_8$, 30° C.) δ: 7.34 (m.4H); 6.98 (m,2H); 6,69 (m,2H); 5.78 (s,2H); 3.14 (sept, 2H); 1.81 (s,6H); 1.20 (d,12H).

EXAMPLE 4 rac-isopropylidene-bis(3-t-butyl-indenyl)zirconium dichloride (a) Synthesis of 2,2-bis(3-tertbutyl-indenyl)propane It was worked according to the procedure described at point (a) of example 1 except that, instead of indene, 200 mmol of 3-tertbutyl-indene was used and that, after the acetone addition, the mixture was stirred under reflux for 4 hours. The temperature of distillation was 145–185° C. The product was isolated as dilithium salt (yield 48%). $^1$H-NMR (THF-d$_8$, 30° C.) δ: 8.17 ("t",4H) 6.95 (mm,4K) {ABCD} 7.36 (s,2H) 2.70 (s,6H,>CMe$_2$) 2.19 (s, 18H,—CMe$_3$).

(b) Synthesis of rac-isopropylidene-bis(3-tertbutyl-indenyl) zirconium dichloride It was worked according to the procedure described at point (c) of example 1 except that, instead of 2,2-bis(3-trimethylsilyl-indenyl)propane, 20 mmol of the dilithium salt of 2,2-bis(3-tertbutyl-indenyl)propane was used, and that the product was recrystallized from DME. Pure rac-isopropylidene-bis(3-tertbutyl-indenyl)zirconium dichloride was obtained. $^1$H-NMR (CD$_2$Cl$_2$, 30° C.) δ: 7.75 (m.4H); 7.25 (dd,2H); 6,97 (dd,2H); 5.97 (s,2H); 2.33 (s,6H); 1.37 (s,18H).

EXAMPLE 5 rac-isopropylidene-bis(3-t-butyl-4,5,6,7-tetrahydro-indenyl)zirconium dichloride In a 100 ml glass-autoclave were introduced 0.66 g of rac-isopropylidene-bis(3-t-butyl-indenyl)zirconium dichloride, 40 mg of $PtO_2$ and 50 ml of $CH_2Cl_2$. 5 atm of $H_2$ were pressurized in and the mixture was stirred for 4 hours at room temperature. The mixture was filtered, the filtrate brought to dryness and 0,56 g of a yellow solid was isolated, which was further purified by washing with hexane and $Et_2O$. 0,22 g of a yellow powder were thus obtained. $^1H$-NMR ($CDCl_3$): 5.3(s), 2.6–2.9(m), 2.2–2.4(m), 1.85(s), 1.4–1.8(m), 1.3(s).

EXAMPLE 6 rac-isopropylidene-bis(3-t-butyl-cyclopentadienyl)zirconium dichloride (a) Synthesis of 2,2-bis(3-t-butyl-cyclopentadienyl)propane 10 g of KOH, 150 mmol of t-butyl-cyclopentadiene and 4.35 g of acetone were suspended in 100 ml of DME and the mixture obtained was heated to ref lux and stirred for 2 hours. The mixture was then cooled and treated with 200 ml of water and 100 ml of diethyl ether. The organic phase was separated off, washed with water and dried over $CaCl_2$. The solvent was then evaporated in vacuo and the residue was distilled at a temperature of 145–165° C. The broad fraction was collected and recrystallized (yield 81%). $^1H$-NMR ($CDCl_3$) δ: 6.3–5.7 (m, 4H) 3.0–2.8 (m, 4H) 1.5–1.4 (m, 6H) 1.3–1.2 (m, 18H).

(b) Synthesis of rac-isopropylidene-bis(3-t-butyl-cyclopentadienyl)zirconium dichloride It was worked according to the procedure described at point (c) of example 1 except that, instead of 2,2-bis(3-trimethylsilyl-indenyl)propane, 6.01 g (20 mmol) of 2,2-bis(3-t-butyl-cyclopentadienyl)propane, and that the product was washed with 50 ml of pentane and then recrystallized from ether. 1.97 g of pure rac-isopropylidene-bis(3-t-butyl-cyclopentadienyl)zirconium dichloride was obtained (yield 22%). $^1H$-NMR (THF-$d_8$, 30° C.) δ: 5.65 (t,2H); 5.53 (t,2H); 1.60 (s,6H); 1.23 (s, 8H).

EXAMPLE 7

Isopropylidene-bis(2-methyl-4-t-butyl-cyclopentadienyl)zirconium dichloride (a) Synthesis of 2.2-bis(2-methyl-4-t-butyl-cyclopentadienyl)propane 17.8 g (131 mmol) of 2-methyl-4-t-butyl-cyclopentadiene was added within 0.5 hours under vigorous stirring to a suspension of 10 g of KOH powder in 100 ml of DME. The obtained mixture was heated to reflux. Then 4.8 ml (66 mmol) of acetone was added dropwise within 0.5 hours and the mixture was stirred under reflux for additional 6 hours. The resulting mixture was cooled, treated with 200 ml of diluted phosphoric acid until neutralization and then with 100 ml of diethyl ether. The organic layer was separated, washed with water and dried over $Na_2SO_4$. Then the solvent was removed in vacuo and the residue was distilled under 0.01 torr. The 130–160° C. broad fraction was collected, diluted with 30 ml of $Et_2O$ and treated with 60 ml of a 2.0M solution of n-butyllithium in hexane. White crystalline precipitate of the product was isolated, washed twice by 20 ml of $Et_2O$ and dried in vacuo (yield 60%).

$^1H$-NMR (THF-$d_8$, 30° C.)) δ: 5.52 ("d", 2H); 5.22 ("d", 2H); 3.58 (s, 6H); 1.58 (s, 6H); 1.18 (s, 18H).

(b) Synthesis of isopropylidene-bis(2-methyl-4-t-butyl-cyclopentadienyl)zirconium dichloride 3.24 g (10 mmol) of the product obtained in step (a) was treated with 3.98 g (20 mmol) of trimethylstannylchloride diluted in 50 ml of $Et_2O$. The solution was decanted from LiCl precipitate, the solvent was removed and the residue was diluted with 40 ml of toluene. The resulting solution was treated with 2.33 g (10 mmol) of $ZrCl_4$ and the mixture was stirred until the $ZrCl_4$ was dissolved. Then the solvent was removed and the residual solid was recrystallized from heptane. A 1:1 rac-/meso-mixture of isopropylidene-bis(2-methyl-4-t-butyl-cyclopentadienyl)zirconium dichloride was obtained (yield 87%). Recrystallization from DME yields a 2:1 rac-/meso-mixture. $^1H$-NMR ($CD_2Cl_2$; 30° C.) rac-form δ: 6.29 (d, J=3.0 Hz, 2H); 5.51 (d, J=3.0 Hz, 2H) [cyclopentadienyl ring]; 2.16 (s, 6H, —$CH_3$ in ring); 1.91 (s, 6H, >C($CH_3$)$_2$); 1.28 (s, 18H, —C($CH_3$)$_3$). meso-form δ: 6.08 (d, J=3.0 Hz, 2H); 5.65 (d, 2H) [cyclopentadienyl ring]; 2.29 (s, 6H, —$CH_3$ in ring); 2.01, 1.88 (s, 2×3H, >C($CH_3$)$_2$); 1.23 (s, 18H, —C($CH_3$)$_3$). $^{13}C$-NMR (-"-) δ: 145.5; 118.2 [quat. C in ring]; 120.7; 106.2; 100.2 [tert. C in ring]; 37.0; 33.0; [>C<]; 30.1 [C($CH_3$)$_3$]; 24.2 [>C($CH_3$)$_2$].

EXAMPLE 8 pseudorac-benzilidene-bis(indenyl)zirconium dichloride (a) Synthesis of bis(indenyl)phenylmethane It was worked according to the procedure described at point (a) of example 1 except that, instead of acetone, 100 mmol of benzaldeide was used and that, after the benzaldeide addition, the mixture was stirred under reflux for 5 hours. The temperature of distillation was 140–170° C. The collected fraction was recrystallized from a heptane (yield 60%). $^1H$-NMR (acetone-$d_6$, 30° C.) δ: 7.52–7.18 {mm, 13H,} 6.05 (q,2H,=CH—) 5.39 (m,1H,>CH—) 3.40 (br.s., 4H,—$CH_2$—). $^{13}C$-NMR ($CD_2Cl_2$, 30° C.) δ145.6; 145.1; 141.5 (=C<) 131.8; 129.3; 128.7; 127.0; 126.2; 124.1; 120.2 (=CH—) 44.5 (>CH—) 38.1 (—$CH_2$—).

(b) Synthesis of pseudorac-benzilidene-bis(indenyl)zirconium dichloride

It was worked according to the procedure described at point (c) of example 1 except that, instead of 2,2-bis(3-trimethylsilyl-indenyl)propane, 20 mmol of the dilithium salt of bis(indenyl)phenylmethane was used, and that the product was recrystallized from DME. pseudorac-benzilidene-bis(indenyl)zirconium dichloride was obtained (due to unsimmetry of the bridge, the anti-isomer can not be the exact rac- isomer). $^1H$-NMR ($CD_2Cl_2$, 30° C.) δ: 7.84–7.12 (groups of multiplets,12H); 6.76 (t,1H); 6.70 (d,1H); 6.60 (d,1H); 6.11 (two doublets,1H+1H); 6.51 (br.s, 1H).

Polymerization of Propylene

Modified Methylalumoxane (M-MAO)

A commercial product (ALBEMARLE) was used as such in a Isopar C solution (62 g of Al/l).

EXAMPLES 9–10

A 1 l steel autoclave, equipped with a jacket, a stirrer system and a resistance heater connected to a thermostat for temperature control, and cleaned beforehand with a solution of $AliBu_3$ in hexane and then dried at 60° C. under a nitrogen stream, was charged with 0.4 l of propylene. The autoclave is then brought to the desired temperature, and 2.25 ml of a solution of M-MAO in Isopar C and 0.5 ml of toluene containing 1 mg of the metallocene of Example 1, aged for 10 minutes, are added thereto. The polymerization is carried out for 1 hour. The polymerization conditions and the data relating to the characterization of the obtained polymers are indicated in Table 1.

EXAMPLES 11–17

The procedure followed was as described in Examples 9–10, using a 2.3 l steel autoclave, equipped with a jacket, stirrer and resistance heater, and connected to a thermostat for temperature control. The polymerization conditions and the data relating to the characterization of the obtained polymers are indicated in Table 1.

EXAMPLES 18–22

The procedure followed was as described in Examples 9–10, except that the metallocene of Example 4 was used. The polymerization conditions and the data relating to the characterization of the obtained polymers are indicated in Table 1.

EXAMPLES 23–25

The procedure followed was as described in Examples 18–22, except that the metallocene of Example 4 was used as a 7:3 rac/meso mixture obtained before recrystallization. The polymerization conditions and the data relating to the characterization of the obtained polymers are indicated in Table 1.

EXAMPLES 26–27

The procedure followed was as described in Examples 9–10, except that the metallocene of Example 5 was used. The polymerization conditions and the data relating to the characterization of the obtained polymers are indicated in Table 1.

EXAMPLE 28

The procedure followed was as described in Examples 9–10, using 1 mg of the metallocene of Example 6. The polymerization conditions and the data relating to the characterization of the obtained polymers are indicated in Table 1.

EXAMPLE 29

The procedure followed was as described in Examples 11–17, using 1 mg of the metallocene of Example 6. The polymerization conditions and the data relating to the characterization of the obtained polymers are indicated in Table 1.

EXAMPLES 30–34

The procedure followed was as described in Examples 9–10, except that the metallocene of Example 7 was used. The polymerization conditions and the data relating to the characterization of the obtained polymers are indicated in Table 1.

EXAMPLES 35–36

The procedure followed was as described in Examples 30–34, except that a 100 litres autoclave was used. The polymerization conditions and the data relating to the characterization of the obtained polymers are indicated in Table 1.

EXAMPLES 37–38

The procedure followed was as described in Examples 9–10, except that 235 g (0.45l) of propylene and 28 g of 1-butene were charged into the autoclave. The metallocene used, the polymerization conditions and the data relating to the characterization of the obtained copolymers are indicated in Table 2.

TABLE 1

| Ex | metallocene | Zr ($\mu$mol) | Al/Zr (mol) | T (°C.) | yield (g) | activity (Kg$_{pol}$/ mmol$_{Zr}$h) | I.V. (dL/g) | Mw/Mn | XSRT (% w) | T$_m$ (°C.) | $\Delta H_m$ (J/g) | m (%) | mmmm (%) | 2,1 insertions |
|---|---|---|---|---|---|---|---|---|---|---|---|---|---|---|
| 9 | Me$_2$C(3-TMS-Ind)$_2$ZrCl$_2$ | 1.72 | 1500 | 70 | 45.0 | 26.2 | 0.53 | | | 126 | 65 | 92.82 | 82.70 | 0 |
| 10 | " | 1.73 | 3000 | 50 | 66.1 | 38.1 | 0.78 | | | 140 | 77 | 94.81 | 87.36 | 0 |
| 11 | " | 6.93 | 3000 | 40 | 98.4 | 14.2 | 0.77 | | | 139 | 76 | 95.94 | 90.06 | 0 |
| 12 | " | 6.93 | 3000 | 30 | 49.4 | 7.1 | 0.98 | | <1 | 142 | 73 | 96.55 | 91.51 | 0 |
| 13 | " | 10.40 | 3000 | 20 | 93.6 | 9.0 | 1.04 | | | 144 | 82 | 97.23 | 93.18 | 0 |
| 14 | " | 10.40 | 500 | 20 | 10.6 | 1.0 | 1.27 | | | 146 | 77 | | | |
| 15 | " | 10.40 | 1000 | 20 | 24.2 | 2.3 | 1.35 | | | 145 | 78 | | | |
| 16 | " | 10.40 | 1500 | 20 | 66.8 | 6.4 | 1.22 | | | 145 | 81 | | | |
| 17 | " | 3.47 | 10000 | 20 | 23.3 | 6.7 | 1.05 | | | 146 | 68 | | | |
| 18 | Me$_2$C(3-tBu-Ind)$_2$ZrCl$_2$ | 0.18 | 8000 | 70 | 20.2 | 109.9 | 0.33 | | | 140 | 88 | 95.50 | 89 | 0 |
| 19 | " | 0.18 | 8000 | 50 | 22.9 | 124.6 | 0.89 | | | 153 | 95 | 97.90 | 94.80 | 0 |
| 20 | " | 0.37 | 8000 | 40 | 41.3 | 112.4 | 1.18 | | | 156 | 95 | 98.19 | 95.52 | 0 |
| 21 | " | 0.37 | 8000 | 30 | 25.3 | 68.8 | 1.74 | | | 157 | 94 | 98.70 | 96.78 | 0 |
| 22 | " | 0.37 | 8000 | 20 | 11.8 | 32.0 | 2.75 | | | 158 | 87 | 98.75 | 96.89 | 0 |
| 23 | Me$_2$C(3-tBu-Ind)$_2$ZrCl$_2$ | 0.37 | 8000 | 60 | 41.3 | 112.4 | 0.53 | | 0.6 | 148 | 97 | | | |
| 24 | " | 0.37 | 8000 | 40 | 30.0 | 81.6 | 1.09 | | 0.5 | 156 | 92 | | | |
| 25 | " | 0.37 | 8000 | 20 | 4.6 | 12.4 | 2.97 | | 0.6 | 159 | 86 | | | |
| 26 | Me$_2$C(3-tBu-H$_4$Ind)$_2$ZrCl$_2$ | 1.81 | 3000 | 70 | 18.6 | 10.3 | wax | | | | | | | |
| 27 | " | 1.81 | 3000 | 50 | 19.1 | 10.5 | wax | | | 100 | 41 | 94.14 | 85.79 | 0 |
| 28 | Me$_2$C(3-tBu-Cp)$_2$ZrCl$_2$ | 2.25 | 3000 | 50 | 34.8 | 15.5 | 0.26 | | | 153 | 108 | 99.77 | 99.44 | 0.35 |
| 29 | " | 9.00 | 3000 | 20 | 16.9 | 1.9 | 0.53 | | | 159 | 96 | | | |
| 30 | Me$_2$C(2-Me-4-tBu-Cp)$_2$ZrCl$_2$ | 0.42 | 8000 | 70 | 58.7 | 138.8 | 0.42 | 2.18 | 0.4 | 157 | 112 | 9.50 | 98.74 | 0.23 |
| 31 | " | 0.42 | 8000 | 60 | 50.7 | 119.9 | 0.69 | 1.95 | | 160 | 106 | | | |
| 32 | " | 0.42 | 8000 | 50 | 30.7 | 72.6 | 0.89 | 1.90 | 0.2 | 162 | 106 | 99.78 | 99.45 | 0.16 |
| 33 | " | 0.42 | 8000 | 35 | 10.2 | 24.2 | 1.51 | 2.05 | | 164 | 96 | | | |
| 34 | " | 0.42 | 8000 | 20 | 3.9 | 9.3 | 2.18 | | 0.2 | 165 | 89 | 99.86 | 99.65 | 0.02 |
| 35 | " | 59.24 | 2000 | 50 | 3190 | 78.5 | 0.92 | 2.41 | | 160 | 115 | 99.68 | 99.20 | 0.14 |
| 36 | " | 122.71 | 2000 | 35 | 3281 | 24.2 | 1.7 | 2.35 | | 162 | 113 | 99.74 | 99.35 | 0.07 |

TABLE 2

| Example | metallocene | Zr (μmol) | Al/Zr (mol) | T (°C.) | yield (g) | activity (Kg$_{pol}$/mmol$_{Zr}$h) | I.V. (dL/g) | Mw/Mn | XSRT (% w) | T$_m$ (°C.) | ΔH$_m$ (J/g) | 1-butene (mol %) |
|---|---|---|---|---|---|---|---|---|---|---|---|---|
| 37 | Me$_2$C(2-Me-4-tBu-Cp)$_2$ZrCl$_2$ | 0.42 | 8000 | 40 | 22.7 | 113.7 | 1.43 | 1.93 | 0.2 | 143 | 77 | 5.52 |
| 38 | Me$_2$C(3-tBu-Ind)$_2$ZrCl$_2$ | 0.37 | 8000 | 40 | 4.77 | 23.9 | 1.01 | 1.88 | 0.8 | 133 | 73 | 6.98 |

We claim:

1. A metallocene compound of formula (I):

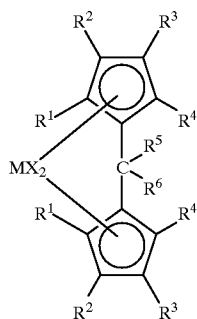

wherein $R^1$, $R^3$, and $R^4$, which can be identical or different, are hydrogen atoms or $C^1$–$C_{20}$-alkyl, $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain silicon or germanium atoms, provided that $R^3$ is not a hydrogen atom;

$R^2$ is a hydrogen atom;

$R^5$ is a hydrogen atom or a —CHR$^7$R$^8$ group;

$R^6$ is a $C_6$–$C_{20}$ aryl radical or a —CHR$^9$R$^{10}$ group;

$R^5$ and $R^6$ can form a ring having from 3 to 8 carbon atoms which can contain hetero atoms;

$R^7$, $R^8$, $R^9$, and $R^{10}$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain hetero atoms and two $R^7$, $R^8$, $R^9$, and $R^{10}$ substituents can form a ring having 3 to 8 carbon atoms which can contain hetero atoms;

M is an atom of a transition metal selected from the group consisting of groups 4, 5, and 6, in the Periodic Table of the Elements (new IUPAC version);

the X substituents, which can be identical or different, are hydrogen atoms, halogen atoms, or —R, —OR, —SR, —NR$_2$ or —PR$_2$ groups, wherein the R substituents are $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain silicon or germanium atoms;

with the proviso that, when the $R^1$ and $R^4$ substituents are hydrogen atoms and the $R^5$ and $R^6$ substituents are methyl groups, then the $R^3$ substituents are other than an isopropyl or tert-butyl group.

2. The metallocene compound according to claim 1 wherein the $R^1$ substituents are different from hydrogen atoms.

3. The metallocene compound according to claim 1, wherein the $R^3$ substituents are carbon, silicon or germanium atoms substituted with three alkyl, cycloalkyl, aryl, alkylaryl or arylalkyl groups each having 1 to 10 carbon atoms.

4. The metallocene compound according to claim 1, wherein the $R^4$ substituents are hydrogen atoms.

5. The metallocene compound according to claims 1, wherein the transition metal M is selected from the group consisting of titanium, zirconium and hafnium.

6. The metallocene compound according to claim 1, wherein the hetero atoms are selected from the group consisting of nitrogen, phosphorous, oxygen and sulphur.

7. The metallocene compound according to claim 1, wherein the X substituents are chlorine atoms or methyl groups.

8. A metallocene compound of formula (II):

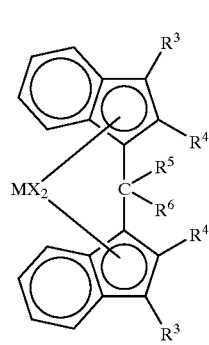

and the corresponding bis-4,5,6,7-tetrahydroindenyl compound, wherein $R^3$, and $R^4$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain silicon or germanium atoms, provided that $R^3$ is not a hydrogen atom;

$R^5$ is a hydrogen atom or a —CHR$^7$R$^8$ group;

$R^6$ is a $C_6$–$C_{20}$ aryl radical or a —CHR$^9$R$^{10}$ group;

$R^5$ and $R^6$ can form a ring having from 3 to 8 carbon atoms which can contain hetero atoms;

$R^7$, $R^8$, $R^9$, and $R^{10}$, which can be identical or different, are hydrogen atoms or $C_1$–$C_{20}$-alkyl, $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain hetero atoms and two $R^7$, $R^8$, $R^9$, and $R^{10}$ substituents can form a ring having 3 to 8 carbon atoms which can contain hetero atoms;

M is an atom of a transition metal selected from the group consisting of groups 4, 5, and 6, in the Periodic Table of the Elements (new IUPAC version); and the X substituents, which can be identical or different, are hydrogen atoms, halogen atoms, or —R, —OR, —SR, —NR$_2$ or —PR$_2$ groups, wherein the R substituents are $C_1$–$C_{20}$-alkyl, $C_3$–$C_{20}$-cycloalkyl, $C_2$–$C_{20}$-alkenyl, $C_6$–$C_{20}$ aryl, $C_7$–$C_{20}$-alkylaryl, or $C_7$–$C_{20}$ arylalkyl groups which can contain silicon or germanium atoms.

9. The metallocene compound according to claim 8, wherein the $R^3$ substituents are carbon, silicon or germanium atoms substituted with three alkyl, cycloalkyl, aryl, alkylaryl or arylalkyl groups each having 1 to 10 carbon atoms.

10. The metallocene compound according to claim 8, wherein the $R^4$ substituents are hydrogen atoms.

11. The metallocene compound according to claim 8, wherein the transition metal M is selected from the group consisting of titanium, zirconium and hafnium.

12. The metallocene compound according to claim 8, wherein the hetero atoms are selected from the group consisting of nitrogen, phosphorous, oxygen and sulphur.

13. The metallocene compound according to claim 8, wherein the X substituents are chlorine atoms or methyl groups.

14. A process for the preparation of a metallocene compound of formula (I):

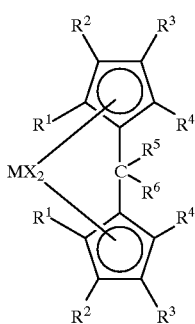

(I)

wherein $R^1$, $R^3$, and $R^4$, which can be identical or different, are hydrogen atoms or $C_1-C_{20}$-alkyl, $C_3-C_{20}$-cycloalkyl, $C_2-C_{20}$-alkenyl, $C_6-C_{20}$ aryl, $C_7-C_{20}$-alkylaryl, or $C_7-C_{20}$ arylalkyl groups which can contain silicon or germanium atoms, provided that $R^3$ is not a hydrogen atom;

$R^2$ is a hydrogen atom;

$R^5$ is a hydrogen atom or a —$CHR^7R^8$ group;

$R^6$ is a $C_6-C_{20}$ aryl radical or a —$CHR^9R^{10}$ group;

$R^5$ and $R^6$ can form a ring having from 3 to 8 carbon atoms which can contain hetero atoms;

$R^7$, $R^8$, $R^9$, and $R^{10}$, which can be identical or different, are hydrogen atoms or $C_1-C_{20}$-alkyl, $C_3-C_{20}$-cycloalkyl, $C_2-C_{20}$-alkenyl, $C_6-C_{20}$ aryl, $C_7-C_{20}$-alkylaryl, or $C_7-C_{20}$ arylalkyl groups which can contain hetero atoms and two $R^7$, $R^8$, $R^9$, and $R^{10}$ substituents can form a ring having 3 to 8 carbon atoms which can contain hetero atoms;

M is an atom of a transition metal selected from the group consisting of groups 4, 5, and 6, in the Periodic Table of the Elements (new IUPAC version);

the X substituents, which can be identical or different, are hydrogen atoms, halogen atoms, or —R, —OR, —SR, —$NR_2$ or —$PR_2$ groups, wherein the R substituents are $C_1-C_{20}$-alkyl, $C_3-C_{20}$ cycloalkyl, $C_2-C_{20}$-alkenyl, $C_6-C_{20}$ aryl, $C_7-C_{20}$-alkylaryl, or $C_7-C_{20}$ arylalkyl groups which can contain silicon or germanium atoms;

with the proviso that, when the $R^1$ and $R^4$ substituents are hydrogen atoms and the $R^5$ and $R^6$ substituents are methyl groups, then the $R^3$ substituents are other than an isopropyl or tert-butyl group, said process comprising the reaction of the corresponding bis-cyclopentadienyl ligands of formula (III):

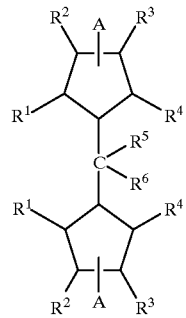

wherein $R^1$, $R^2$, $R^3$, $R^4$, $R^5$, $R^6$ are defined as above, the double bonds of the cyclopentadienyl rings in the ligands of formula (III) being in any of the allowed positions, and A is a suitable leaving group, with a compound of the formula $MX_4$, wherein M and X are as defined above.

15. A process for the preparation of a metallocene compound of formula (II):

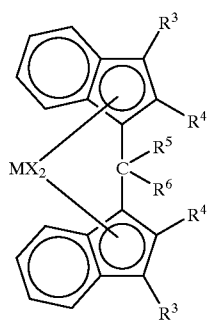

(II)

wherein $R^3$, and $R^4$, which can be identical or different, are hydrogen atoms or $C_1-C_{20}$-alkyl, $C_3-C_{20}$-cycloalkyl, $C_2-C_{20}$-alkenyl, $C_6-C_{20}$ aryl, $C_7-C_{20}$-alkylaryl, or $C_7-C_{20}$ arylalkyl groups which can contain silicon or germanium atoms, provided that $R^3$ is not a hydrogen atom;

$R^5$ is a hydrogen atom or a —$CHR^7R^8$ group;

$R^6$ is a $C_6-C_{20}$ aryl radical or a —$CHR^9R^{10}$ group;

$R^5$ and $R^6$ can form a ring having from 3 to 8 carbon atoms which can contain hetero atoms;

$R^7$, $R^8$, $R^9$, and $R^{10}$, which can be identical or different, are hydrogen atoms or $C_1-C_{20}$-alkyl, $C_3-C_{20}$-cycloalkyl, $C_2-C_{20}$-alkenyl, $C_6-C_{20}$ aryl, $C_7-C_{20}$-alkylaryl, or $C_7-C_{20}$ arylalkyl groups which can contain hetero atoms and two $R^7$, $R^8$, $R^9$, and $R^{10}$ substituents can form a ring having 3 to 8 carbon atoms which can contain hetero atoms;

M is an atom of a transition metal selected from the group consisting of groups 4, 5, and 6, in the Periodic Table of the Elements (new IUPAC version);

the X substituents, which can be identical or different, are hydrogen atoms, halogen atoms, or —R, —OR, —SR, —$NR_2$ or —$PR_2$ groups, wherein the R substituents are $C_1-C_{20}$-alkyl, $C_3-C_{20}$-cycloalkyl, $C_2-C_{20}$-alkenyl, $C_6-C_{20}$ aryl, $C_7-C_{20}$-alkylaryl, or $C_7-C_{20}$ arylalkyl groups which can contain silicon or germanium atoms;

with the proviso that, when the $R^4$ substituents are hydrogen atoms and the $R^5$ and $R^6$ substituents are methyl groups, then the $R^3$ substituents are other than an isopropyl or tert-butyl group, said process comprising the reaction of the corresponding bis-cyclopentadienyl ligands of formula (IV):

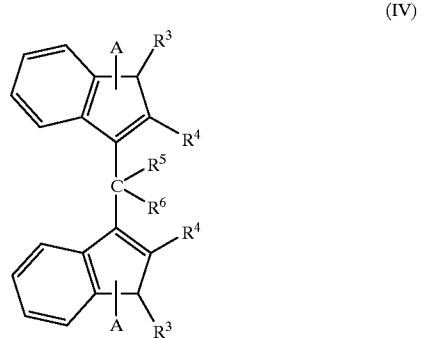

(IV)

wherein $R^3$, $R^4$, $R^5$, $R^6$ are defined as above, the double bonds of the cyclopentadienyl rings in the ligands of formula (IV) being in any of the allowed positions, and A is a suitable leaving group, with a compound of the formula $MX_4$, wherein M and X are as defined above.

* * * * *

UNITED STATES PATENT AND TRADEMARK OFFICE
CERTIFICATE OF CORRECTION

PATENT NO. : 6,051,728
DATED : April 18, 2000
INVENTOR(S) : Luigi Resconi et al.

It is certified that error appears in the above-identified patent and that said Letters Patent is hereby corrected as shown below:

Title page,
OTHER PUBLICATIONS, please change "Oct. 19" to -- Oct. 9 --;

Column 15, claim 1,
Line 51, after "are", insert -- $C_1$-$C_{20}$-alkyl. --;

Column 16, claim 5,
Line 12, change "claims" to -- claim --;

Column 17, claim 14,
Line 37, change "$C_{1-C20}$" to -- $C_1$-$C_{20}$ --;

Column 18, claim 14,
Lines 4-15, change the formula as follows:

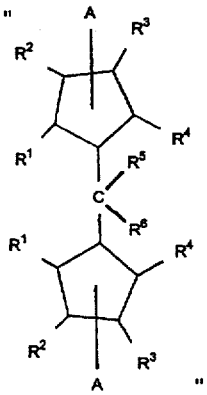 to 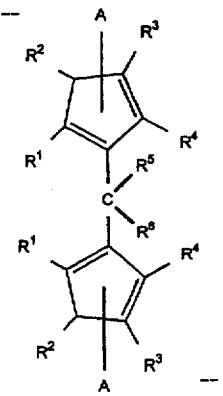

Signed and Sealed this

Fifth Day of February, 2002

Attest:

JAMES E. ROGAN
Director of the United States Patent and Trademark Office

Attesting Officer